United States Patent [19]
Scarbrough

[11] 3,960,145
[45] June 1, 1976

[54] HEAT THERAPY AND SPINAL TRACTION CHAIR

[76] Inventor: Gilbert R. Scarbrough, 126 S. Olive St., Rialto, Calif. 92376

[22] Filed: July 7, 1975

[21] Appl. No.: 593,442

[52] U.S. Cl. .................... 128/68.1; 128/71
[51] Int. Cl.² ........................................ A61F 5/00
[58] Field of Search ............... 128/71, 68.1, 75, 376, 128/377, 24.2, 24.1; 297/180

[56] References Cited
UNITED STATES PATENTS

| | | | |
|---|---|---|---|
| 1,173,306 | 2/1916 | Pool | 128/68.1 |
| 1,356,365 | 10/1920 | Hosmer | 128/75 |
| 2,583,816 | 1/1952 | Butler | 128/377 X |
| 2,940,442 | 6/1960 | Wilhelm | 128/75 |
| 2,949,152 | 8/1960 | Hipps et al. | 128/75 X |
| 3,738,702 | 6/1973 | Jacobs | 297/380 |

*Primary Examiner*—Lawrence W. Trapp
*Attorney, Agent, or Firm*—Dana E. Keech

[57] ABSTRACT

An upholstered arm chair embodying in the structure thereof a water heating tank underlying and directly heating the seat cushion of the chair and hydraulic heating pads forming the surface cushions of the back and arm rests of the chair, and automatic thermostat regulated electric means for heating the water in said tank and maintaining the same at a selected temperature and for circulating said water from said tank through said arm and back heating pads and then back to said tank. The chair also provides means for applying linear traction to the spine of the patient while heat therapy treatment is being adminstered.

3 Claims, 4 Drawing Figures

HEAT THERAPY AND SPINAL TRACTION CHAIR

SUMMARY OF THE INVENTION

It is a principal object of the invention to provide what is commonly referred to as an "Overstuffed" arm chair which is an attractive piece of furniture in any home or doctor's office but which embodies concealed beneath the outer fabric of the upholstery, facilities for administering heat therapy to a patient sitting therein.

Another object is to provide such a chair which also offers, normally concealed beneath its outer fabric covering, a means for applying linear spinal traction to a patient while seated in said chair to receive a heat therapy treatment.

A yet further object is to provide in such a chair a means accessible from the rear of the chair for measuring and applying tension of various degrees to the spine of the patient and for modifying said tension during the treatment so as to make this at all times comfortable for the patient.

DETAILED DESCRIPTION OF THE PREFERRED EMBODIMENT

Figure 1:
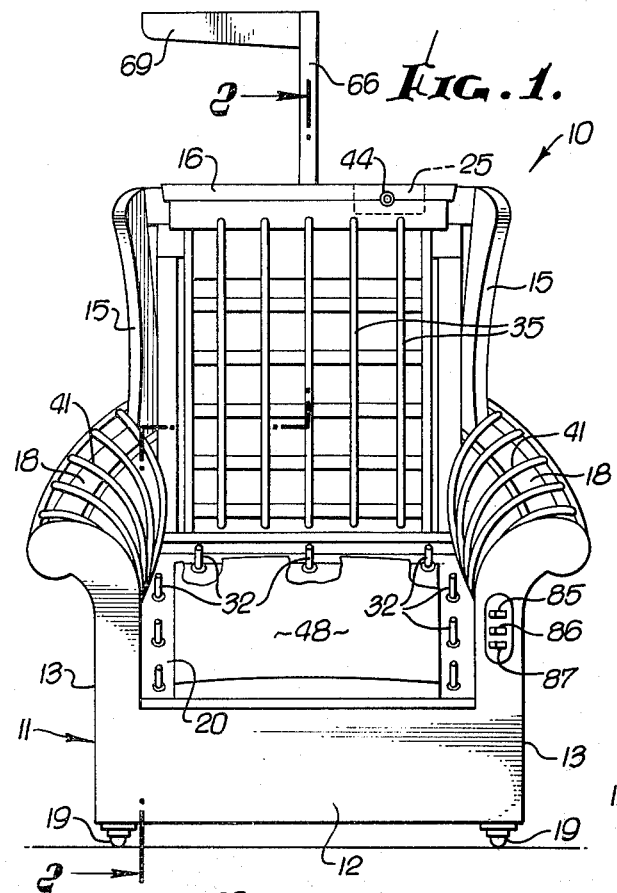
FIG. 1 is a perspective front view, partly broken away of a preferred embodiment of the invention and with the outer fabric and arm and back heating pads removed.

The invention preferably embodies an upholstered arm chair 10, including a solid rectangular frame 11, having a front wall 12 and side walls 13, which are connected together by a horizontal flat plate 14 at their rear ends. Extending upwardly from rear end portions of said side walls are side frame members 15 which are connected together at their upper ends by a cross member 16 to form a chair back frame 17. Extending forwardly from the vertical side frame members 15 and downwardly to the seat level of the rectangular wooden frame 11, are arm rest frames 18.

Fixed to the bottom of the four corners of the arm chair frame 11 are casters 19 for rollably supporting the chair 10. Suitably supported within the upper portion of the wooden base frame 11 is a rectangular water heating tank 20. Mounted in a suitable recess provided in upper horizontal back cross member 16 is a manifold reservoir 25 to which hot water is delivered through a vertical plastic tube 26 which connects to the discharge end of an electric motor rotary pump unit 27 which is secured to the bottom horizontal back cross plate 14.

The tank 20 is provided with two electric heating elements 28 and 29 which are automatically controlled by electronic thermostats 30 and 31 respectively.

The tank 20 is provided with upwardly extending return drain pipes 32 which make tightly sealed connections with the tank and extend upwardly therefrom along both side and back edges of said tank.

The chair back frame 17 includes horizontal bars 33 which are penetrated with a series of horizontal holes in which are mounted horizontal plastic tubes 34 on the forward ends of which are fixed five plastic tubes 35 which flexibly support a rearwardly inclined polyethylene bag containing porous packing material so as to form a back heating pad 40.

Each of the arm rest frames 18 embodies a bag supporting grid 41 similar to the grid formed by the plastic tubes 34 and 35 of the chair back frame 17. Mounted on the arm rest frames 18 to overlie the bag supporting grids 41 are arm heating pads 42. Incorporated within upper edge portions of the heating pad 40 and the heating pads 42 are perforated copper tubes 43, the outer ends of which connect respectively with hot water delivery tubes 44, 45 and 46 which connect with and receive hot water from the manifold reservoir 25.

The lower edges of back heating pad 40 and arm heating pads 42 make tight sealed connections with the upper ends of return water drain pipes 32 through which water deliverd into the upper ends of pads 40 and 42 drains back downward into the water heating tank 20. Connecting water tank 20 to the inlet of pump 27 is a pipe 50.

Figure 3:
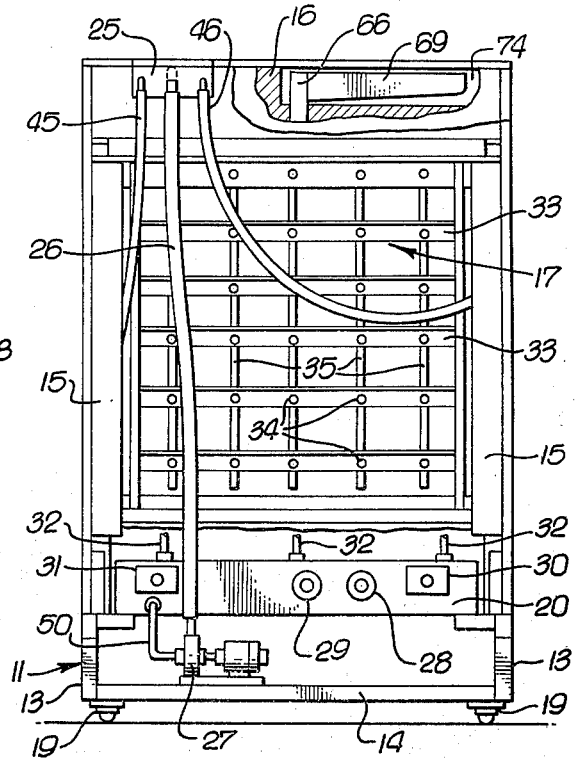
FIG. 3 is a fragmentary rear elevational view of FIG. 1 showing the inner structure as this appears before this is largely covered by upper, middle and lower trim plates (seen in FIG. 4).

Resting on top of the tank 20 and the frame front wall 12 is a thin fabric-covered spring cushioned seat 48 which readily transmits heat radiating upwardly from tank 20 to a patient sitting on said seat. The open back side of the inner structure of the arm chair 10 shown in FIG. 3 is mostly coverd by upper, middle and lower aluminum trim sheets 55, 56 and 57, the latter of which sheets has an inwardly bent wide upper flange 58. Formed centrally in an upper portion of the middle trim plate 56 is a slot 59. Fixed to the rear surface of said middle plate is a vertical guide 60 having a central slot 61 in which a spring scale 62 is slideably mounted. Pivotally mounted in axially offset but co-planar relation to the back face of middle plate 56 is a pair of flanged pulleys 63 and 64.

Fixed centrally on flange 58 is a socket 65, while formed co-axially with said socket in top cross member 16 of the chair back fraame 17 are guide holes for rotatably receiving upper and lower telescopically sliding tubes 66 and 67 of a telescopic mast 68.

Fixed on the upper end of the upper telescopic tube 66 is a boom 69 having mounted therein co-planar flanged pulleys 70 and 71. The telescopic mast 68 is provided with a vertical series of latch holes 72 which are adapted to be engaged by spring biased buttons 73 for the purpose of latching the upper telescopic tube 66 in any desired vertical position within the lower telescopic tube 67.

It is also to be noted in FIG. 3 that a recess 74 is provided in the upper face of chair back frame 17 to conceal the boom 69 when the upper telescopic tube 66 is swung into alignment with the chair back and properly lowered as shown in FIG. 3.

Fixed on the trim plate flange 58 is a small manually actuated ratchet winch 75 which is connected by a light wire cable 76 to the lower end of spring scale 62. The upper end of said scale is connected to a light wire cable 77 which is trained upwardly around flanged pulleys 63 and 64, 70 and 71 and is then connected at its outer end to a head traction harness 78 which is adapted to be secured to the head of the patient 49.

Preferably mounted on the front face of one of the arm rest frames 18 and shown in FIG. 1 are three manual switches 85, 86 and 87 which individually control the electric circuits for turning on or off respectively the electric motor driven pump unit 27, electric water heating unit 28 and the electric water heating unit 29.

When the structure of the arm chair 10 of the invention has been completed as above described, it is covered in its entirety with a suitable upholstering fabric exactly in the same manner as an ordinary overstuffed arm chair. When this is done, it is not possible to distinguish the overstuffed chair 10 from one of the other of the styles of overstuffed chair commonly in use in office and homes, excepting for the fact that the chair 10 necessarily requires that it be connected by an electric cord with a wall service outlet for electrifying the same.

OPERATION

Figure 2:
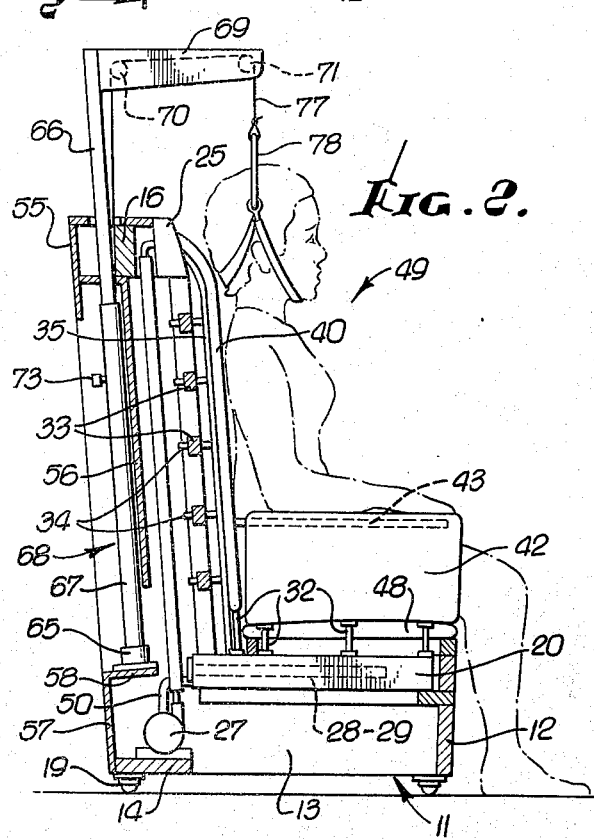
FIG. 2 is a vertical sectional view of the invention taken on the line 2—2 of FIG. 1 and showing all three heating pads in place and the seat occupied by a patient undergoing spinal traction and heat therapy.

In preparing the chair 10 of the invention for use by a patient 49, it is preferable to reheat the chair for approximately a half hour by setting the thermostats 30 and 31 at the desired temperatures and turning on the electric switches 85, 86 and 87. This heats the water in the tank 20 rapidly and also distributes water through the manifold reservoir 25 to upper ends of the back heating pad 40 and the two arm heating pads 42. With the patient now seated in the chair, leaning backwardly against the back heating pad 40, the telescopic mast 68 is adjusted for height with the boom 69 extending forwardly over the head of the patient after which the spinal traction harness 78 is fitted under the chin and back of the head of the patient as shown in FIG. 2. The ratchet winch 75 is now manually actuated to pull down on the spring scale 62 until this registers the desired tension to be applied by the harness 78 to the spine of the patient or until the patient indicates that the maximum degree of tension which is comfortable has been thus applied.

While the treatment is going on, the patient rests his or her arms on the arm heating pads 42 and if desired is furnished with a covering blanket to retain the heat close around the body and legs and arms throughout the therapy treatment.

Should it be more comfortable to the patient, an ottoman is provided for supporting the legs of the patient horizontally or at a slight inclination during the course of the treatment, although such an ottoman is not shown in the drawings.

Figure 4:
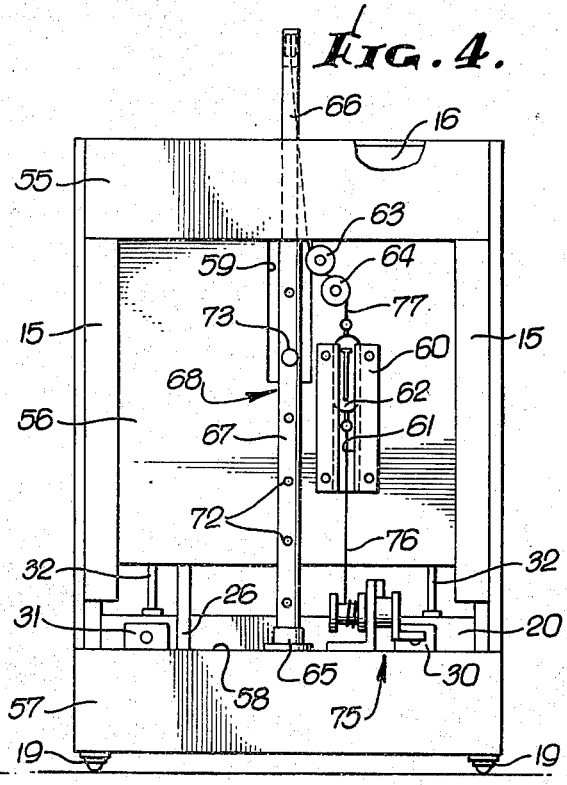
FIG. 4 is a rear elevational view of the invention illustrating the spinal traction actuating mechanism.

Access to the operative elements of the equipment visible in FIG. 4 is made available by suitable openings provided in the fabric covering the back of the chair 10, and preferably controlled by zippers.

I claim:

1. An upholstered arm chair, embodying:

seat supporting, arm supporting, and back supporting structures;

a water heating tank underlying and heating the seat supporting structure of the chair;

heating pads embodied in said back supporting and arm supporting structures of said chair and located near the surface thereof, said heating pads comprising watertight envelopes containing flow retarding fibrous packing material therein but permitting ready circulation of hot water through said pads;

means for automatically circulating water from said heating tank through said heating pads and then returning said water to said tank; and means for maintaining the water in said tank at a wide range of optional selected temperatures.

2. A combination as recited in claim 1 wherein spinal traction means is normally concealed in said overstuffed chair but readily extensible therefrom, said means including a mast having a boom at its upper end;

means for vertically adjusting said mast to support said boom at various heights above the head of a patient seated in said chair;

harness means suspended from said boom for securing to the head of a patient; and cable and pulley means normally concealed within said chair for applying vertical tension to said harness means and thus apply linear traction to the spine of the patient seated in said chair.

3. A combination as recited in claim 2 wherein said harness is connected by a cable controlled by suitable flanged pully means and connected to a spring scale registering the amount of tension applied to said cable; and a manual winch to which said cable is terminally connected and by which the desired tension is applied through said cable to said patient as indicated by the degree of tension registered by said scale.

* * * * *